United States Patent
Favero et al.

(10) Patent No.: US 12,030,832 B2
(45) Date of Patent: Jul. 9, 2024

(54) DIALKYL TIN OXIDE COMPOSITION AND PROCESS FOR PRODUCING 2-DIMETHYLAMINOETHYL (METH)ACRYLATE

(71) Applicant: SNF GROUP, Andrezieux Boutheon (FR)

(72) Inventors: Cédrick Favero, Andrezieux Boutheon (FR); Johann Kieffer, Andrezieux Boutheon (FR); Nicolas Boisse, Taixing (CN); Bruno Michel, Andrezieux Boutheon (FR); Jing Ling, Taixing (CN)

(73) Assignee: SNF GROUP, Andrezieux Boutheon (FR)

(*) Notice: Subject to any disclaimer, the term of this patent is extended or adjusted under 35 U.S.C. 154(b) by 601 days.

(21) Appl. No.: 17/198,573

(22) Filed: Mar. 11, 2021

(65) Prior Publication Data

US 2021/0309605 A1  Oct. 7, 2021

(30) Foreign Application Priority Data

Apr. 1, 2020 (CN) .......................... 202010251025.4

(51) Int. Cl.
| | |
|---|---|
| *C07C 213/06* | (2006.01) |
| *B01J 19/28* | (2006.01) |
| *B01J 31/22* | (2006.01) |
| *B01J 35/23* | (2024.01) |
| *B01J 35/30* | (2024.01) |
| *B01J 37/00* | (2006.01) |
| *C07C 219/08* | (2006.01) |
| *C08F 20/34* | (2006.01) |
| *C07C 19/08* | (2006.01) |

(52) U.S. Cl.
CPC ............ *C07C 213/06* (2013.01); *B01J 19/28* (2013.01); *B01J 31/2213* (2013.01); *B01J 35/23* (2024.01); *B01J 35/393* (2024.01); *B01J 37/0036* (2013.01); *C07C 219/08* (2013.01); *C08F 20/34* (2013.01); *B01J 2219/1946* (2013.01); *B01J 2231/49* (2013.01); *B01J 2531/42* (2013.01)

(58) Field of Classification Search
CPC ...... C07C 213/06; C07C 219/08; B01J 19/28; B01J 31/2213; B01J 35/0013; B01J 35/006; B01J 37/0036; C08F 20/34
See application file for complete search history.

(56) References Cited

U.S. PATENT DOCUMENTS

| | | |
|---|---|---|
| 3,642,877 A | 2/1972 | Jayawant |
| 7,078,560 B2 | 7/2006 | Houben et al. |
| 7,268,251 B2 | 9/2007 | Geisendoerfer et al. |
| 8,186,871 B2 | 5/2012 | Pich et al. |
| 2012/0123147 A1 | 5/2012 | Mullen et al. |
| 2012/0123148 A1* | 5/2012 | Paul ................ B01J 31/122 502/155 |
| 2015/0352507 A1 | 12/2015 | Jeronimo et al. |
| 2018/0078913 A1 | 3/2018 | Bonnier et al. |

FOREIGN PATENT DOCUMENTS

| | | | |
|---|---|---|---|
| JP | S59122538 A | * | 7/1984 |
| WO | 2011/107683 A1 | | 9/2011 |
| WO | 2016/156320 A1 | | 6/2016 |

OTHER PUBLICATIONS

Shiobara JPS59122538A (trans.) (Year: 1984).*

* cited by examiner

*Primary Examiner* — Robert C Boyle
*Assistant Examiner* — Patrick Loen Benitez
(74) *Attorney, Agent, or Firm* — Heslin Rothenberg Farley & Mesiti P.C.

(57) ABSTRACT

The invention relates to a new dialkyl tin oxide catalyst composition and its use for the synthesis of amino alkyl (meth)acrylates by transesterification from an alkyl (meth)acrylates and an amino alcohol, and especially 2-dimethylaminoethyl (meth)acrylate.

The invention also relates to polymers made with quaternized amino alkyl (meth)acrylates and use of said polymers in water treatment, sludge dewatering, papermaking process, agriculture, cosmetic and detergency composition, textile process, oil and gas recovery process such as enhanced oil recovery, fracturing, mining operation such as tailings treatment.

5 Claims, No Drawings

DIALKYL TIN OXIDE COMPOSITION AND PROCESS FOR PRODUCING 2-DIMETHYLAMINOETHYL (METH)ACRYLATE

CROSS REFERENCE TO RELATED APPLICATIONS

This application claims priority to Chinese Patent Application Number 202010251025.4 filed on Apr. 1, 2020, the entire contents of which are hereby incorporated herein by reference.

TECHNICAL FIELD

The present invention relates to a new dialkyl tin oxide catalyst composition and its use for the synthesis of amino alkyl (meth)acrylates by transesterification from an alkyl (meth)acrylates and an amino alcohol, and especially 2-dimethylaminoethyl (meth)acrylate.

TECHNICAL BACKGROUND 2-dimethylaminoethyl (meth)acrylate monomer is generally quaternized, for example with methyl chloride, dialkylsulfate or benzylchloride, and then polymerized to produce cationic polymers. These polymers are used in many industries, such as water treatment, papermaking, home and personal care, oil & gas recovery.

It is well-known to catalyze a transesterification reaction with organo-tin compounds. Amongst (meth)acrylic esters of interest, 2-dimethylaminoethyl (meth)acrylate is obtained by transesterification of alkyl(meth)acrylate and dimethylaminoethanol with tin oxide derivatives as catalyst, for example dibutyltin oxide (DBTO). The catalyst's role is to displace the equilibrium to produce more 2-dimethylaminoethyl (meth)acrylate and reduce the impurity formation The alkyl(meth)acrylate can be methyl(meth)acrylate, ethyl(meth)acrylate, propyl(meth)acrylate, butyl(meth)acrylate, 2-ethylhexyl (meth)acrylate. Methyl (meth)acrylate is generally preferred.

In document U.S. Pat. No. 7,268,251, the preparation of (meth)acrylates by transesterification is carried out in presence of a lower titanium alcoholate catalyst. The lower alcoxytitanate, such as tetra isopropyltitanate is not usable as such. A catalyst preparation step is necessary to perform an alcohol exchange with the amino alcohol of interest. This preparation step includes a heating phase at high temperature to remove continuously by distillation under vacuum the lower alcohol generated. This step is complicated to perform, time and energy intensive and generates a waste stream of the lower alcohol to be disposed of.

Another suitable catalyst widely described in the literature as an effective transesterification catalyst for the synthesis of (meth)acrylate ester is the organo tin derivate. In particular, dialkyl tin oxide and dialkyltin dichloride are described, and more especially dibutyl tin oxide (acronym DBTO). Even if DBTO is described as a monomeric molecule, the product self-aggregates to make clusters of different degrees of polymerization.

For example, in document U.S. Pat. No. 3,642,877, DBTO is described as the preferred catalyst for the transesterification between methyl methacrylate and dimethylaminoethanol that occurs in the preparation of dimethyl aminoethyl methacrylate. Water is a well-known catalyst poison since it reacts with DBTO. As a result, reagents are first dried by azeotropic distillation of water with methyl methacrylate, before the DBTO addition. This reagent-drying step is time and energy intensive, it requires an excess of methyl methacrylate and generates waste to be disposed of. It also requires further treatments of the wet distillate, which is a mixture of methyl methacrylate, water and methanol. Moreover, in this process, DBTO is used in a solid form.

Furthermore, it is known from the literature that neither DBTO nor alkyl (meth)acrylate is soluble in amino alcohol. During the course of the transesterification reaction, an induction time exists before the reaction between amino alcohol and (meth)acrylate ester. Such induction time decreases the productivity and therefore increases the production costs.

Without being bound to any theory, it is believed that the induction time is related to the particle size distribution of DBTO. As such, the person skilled in the art tends to reduce the particle size of DBTO to a pulverulent state. However, doing so may create safety risks for the users due to the inhalation of dust containing toxic tin derivatives.

In order to overcome this issue, document U.S. Pat. No. 7,078,560 proposes to pre-activate the organo tin derivative via the preparation of a distannoxane intermediate. A mixture of dialkyl tin oxide and dialkyl tin dichloride reacts with dimethylaminoethanol in a solvent. The dialkyl tin oxide and the dialkyl tin dichloride self-solubilize without heating. However, a step of evaporating the solvent is necessary in order to recover the distannoxane in solid form after filtration. The process disclosed in this document is complex, in particular due to the solvent distillation step and a further filtration step allowing the recovery of the distannoxane material. Moreover, the presence of chloride ions may cause corrosion of the industrial/production equipment.

Document US 2012/0123147A1 discloses the preparation of a mixture of dibutyl tin oxide by dissolving the same in a mixture of alcohol and an alkyl (meth)acrylate ester or with the presence of the aminoalkyl (meth)acrylate ester. This process requires heating the reaction mixture to a high temperature during several hours. In addition, the DBTO content is limited to a maximum amount of 70%.

In view of the above, the prior art describes different methods of preparation of a catalyst for the synthesis of aminoalkyl(meth)acrylate. However, these methods are complex, comprise a large number of steps, and are energy and time intensive. In addition, such processes generate a waste stream distillate to be treated or disposed of.

Moreover, there is a need to improve the productivity of aminoalkyl(meth)acrylate by reducing the induction time when adding solid dialkyl tin oxide in the reaction mixture. Fines particles of dialkyltin oxide also raise problems and risks concerning the exposure of such particles to the users, as well as potential health issues.

DESCRIPTION OF THE INVENTION

The present invention relates to a new, highly concentrated and stable, dialkyl tin oxide catalyst composition and its use for the synthesis of amino alkyl (meth)acrylates by transesterification from an alkyl (meth)acrylates and an amino alcohol.

The present invention also relates to an ecofriendly dialkyl tin oxide preparation process which does not generate wastes and which may be carried out at lower temperatures compared to the known processes.

It has been surprisingly found that a highly concentrated and stable composition, preferably a suspension, of dialkyl tin oxide can be obtained thanks to a specific composition. Such specific composition is advantageously prepared via a specific process.

The present invention relates to a dialkyl tin oxide composition comprising:
- 80% to 90% by weight of dialkyl tin oxide;
- 5% to 10% by weight of at least one alkyl(meth)acrylate ester;
- 5% to 10% by weight of at least one amino alcohol.

The percentages by weight are relative to the weight of the composition.

According to an embodiment, the dialkyl tin oxide composition consists of or consists essentially of:
- 80% to 90% by weight of dialkyl tin oxide;
- 5% to 10% by weight of at least one alkyl(meth)acrylate ester;
- 5% to 10% by weight of at least one amino alcohol.

In this embodiment, the percentages by weight are relative to the total weight of the composition, and the total is 100%.

In the present invention, the alkyl groups of the dialkyl tin oxide may be linear, cyclic (substituted or not) or branched. The alkyl groups bound to the tin may be identical or different from each other. The alkyl groups may have a number of carbon atoms comprised between 2 and 12, preferably between 4 and 8, more preferably the alkyl group is linear and have a number of carbons of 4, 8 or 12.

In the present invention, the alkyl group of the alkyl (meth)acrylate ester may be linear, cyclic (substituted or not) or branched. The alkyl group may have a number of carbon atoms comprised between 1 and 10, preferably between 1 and 8, more preferably between 1 and 4, even more preferably the alkyl group is methyl or ethyl.

In the present invention, the dialkyl tin oxide is preferably dibutyl tin oxide (DBTO).

In the present invention, an amino alcohol corresponds to a chemical compound that contains both hydroxyl (—OH) and amino functional groups on an alkane backbone. The amino functional groups may be primary (—$NH_2$), secondary (—$NHR^1$), or tertiary (—$NR^1R^2$). This definition includes amino alcohols wherein the hydroxyl and the amino functional groups are separated by another chemical group such as an alkyl for example, but does not include amino alcohols wherein the hydroxyl and the amino functional groups are directly linked to each other (hydroxylamine). The alkyl groups $R^1$ and $R^2$ may be identical or different. They may have a number of carbon atoms comprised between 1 and 8, preferably between 1 and 4.

In a preferred embodiment, the dialkyl tin oxide composition is a suspension in which 70% to 95% by weight of dialkyl tin oxide is solubilized, and 5% to 30% by weight of dialkyl tin oxide is in the form of particles suspended in the composition. The percentages by weight are relative to the total amount of dialkyl tin oxide in the composition. Preferably, more than 80% and no more than 95%, more preferably more than 85% and no more than 95% by weight of dialkyl tin oxide is solubilized in the suspension.

The present invention also relates to a process for the production of a dialkyl tin oxide composition comprising the steps of wetting of dialkyl tin oxide particles with a first wetting solution, grinding and/or slicing of the wetted dialkyl tin oxide particles in the presence of a second wetting solution to obtain a composition A (preferably a suspension A), and heating of the resulting composition to obtain a composition B (preferably a suspension B).

The term "wetting" corresponds to a prolonged contact between the dialkyl tin oxide particles and the first or second wetting solution. The first and the second wetting solution are not necessarily aqueous.

The first wetting solution and/or the second wetting solution preferably is an organic solvent.

The first wetting solution and/or the second wetting solution preferably comprises an alkyl(meth)acrylate ester, or an amino alcohol, or a mixture of an alkyl(meth)acrylate ester and an amino alcohol. The first wetting solution and/or the second wetting solution preferably comprises a mixture of an alkyl(meth)acrylate ester and an amino alcohol.

The molar ratio between the alkyl(meth)acrylate ester and the amino alcohol is advantageously comprised between 1:5 and 5:1, preferably between 1:2 and 2:1.

The first wetting solution and the second wetting solution preferably are identical, but may be different.

In a preferred embodiment, the dialkyl tin oxide particles are wetted and grinded and/or sliced in a device comprising:
- a wetting cone in which the dialkyl tin oxide particles are metered, said cone being connected to a primary wetting solution inlet circuit adapted to provide a first wetting solution,
- at the bottom end of the cone:
  - a chamber for grinding and draining the dispersed dialkyl tin oxide particles, comprising:
    - a rotor driven by a motor and equipped with knives,
    - a fixed stator comprising blades,
- over all or part of the periphery of the chamber, a ring fed by a secondary wetting solution circuit adapted to provide a second wetting solution, the ring being in communication with the chamber to ensure that pressurized second wetting solution is sprayed onto the blades of the stator.

This device is preferably a Polymer Slicing Unit (acronym PSU) manufactured by the company SNF, and described in the documents U.S. Pat. No. 8,186,871, WO2011/107683 and WO2016/156320. These three documents, in particular parts that describe the PSU and its use, are incorporated herein by reference.

The composition A is preferably heated at a temperature comprised between 30° C. and 100° C., preferably between 40° C. and 90° C., for a period of time ranging from 1 minute to 600 minutes, preferably from 30 minutes to 180 minutes.

The present invention also relates to a process for the production of aminoalkyl (meth)acrylate by transesterification from an alkyl (meth)acrylates and an amino alcohol, said process comprising the use of the composition according to the invention as a catalyst of the transesterification.

The skilled man knows how to conduct the reaction and may refer to the document US 2012/0123148 for doing so. An advantage of the process of the invention is that such process does not require specific additional steps to carry out the reaction to obtain aminoalkyl (meth)acrylate by transesterification of methyl(meth)acrylate and dimethylaminoethanol with dialkyl tin oxide as a catalyst.

In a preferred embodiment, the process comprises the following steps:
- in a reactor, the addition of at least one amino alcohol, at least one alkyl(meth) acrylate and at least one solvent with a weight ratio of 2-15:2-40:1-5;
- in the same reactor, the addition of the dialkyl tin oxide composition according to the invention, with a weight ratio amino alcohol/dialkyl tin oxide composition ranging from 10:1 to 100:1 to obtain a composition, preferably a suspension;

the increase of the temperature of the resulting composition (preferably a suspension) from 40° C. to 70° C., for a period of time from 30 minutes to 500 minutes, while continuously removing lower alkyl alcohol thanks to an azeotropic evaporation, for recovering aminoalkyl (meth)acrylate;

optionally, purifying the aminoalkyl (meth)acrylate.

The solvent used in the process of the invention is preferably an inert solvent, i.e. a solvent that does not react with the amino alcohol and the alkyl(meth) acrylate. The solvent is typically an alkane having a carbon chain ranging from C6 to C12, which may be linear, cyclic or branched. A preferred solvent is hexane (linear $C_6H_{14}$), which forms an azeotropic mixture with low molecular weight alcohol, especially with methanol.

The purification is preferably made by distillation.

The aminoalkyl (meth)acrylate is preferably 2-dimethylaminoethyl acrylate or 2-dimethylaminoethyl methacrylate.

The present invention also relates to the aminoalkyl (meth)acrylate, and especially to the 2-dimethylaminoethyl (meth)acrylate, obtained according to the process of the invention previously described.

The present invention also relates to a quaternized aminoalkyl (meth)acrylate, and especially to the 2-dimethylaminoethyl (meth)acrylate. The skilled man knows how to perform this quaternization. The quaternization is made for example with dimethylsulfate, diethylsulfate, benzyl chloride or methylchloride, or a mixture thereof, and preferably with methylchloride, to convert the tertiary amine to a quaternary ammonium.

The present invention also relates to a polymer made from the quaternized aminoalkyl (meth)acrylate, and especially from the 2-dimethylaminoethyl (meth)acrylate. The polymer thus comprises at least one monomeric unit comprising the quaternized aminoalkyl (meth)acrylate.

The polymer may be obtained by polymerization of the quaternized 2-dimethylaminoethyl (meth)acrylate and at least one monomer selected in the following list:

non-ionic monomers: acrylamide, methacrylamide, N,N-dimethylacrylamide, N,N-diethylacrylamide, N-vinylpyrrolidone, N-vinylformamide, N-vinyl imidazole, the methacrylates of polyethylene glycol, diacetone acrylamide, N-isopropylacrylamide, 2-hydroxyethyl acrylate, 2,3-dihydroxypropyl acrylate, 2-hydroxyethyl methacrylate, 2,3-dihydroxypropyl methacrylate,N-tert-butylacrylamide, and their mixtures, anionic monomers: acrylic acid, 2-acrylamido-2-methylpropane sulfonic acid (ATBS), methacrylic acid, itaconic acid, maleic acid, ally sulfonate, non-salified, partially or completely salified, and their mixtures, cationic monomers: diallyldimethylammonium chloride (DADMAC), acrylamido dialkylaminopropyl, methacrylamido dialkylaminopropyl, dialkylamino alkyl methacrylate, dialkylamino alkyl acrylate, dimethylamino alkyl methacrylate, dimethylamino alkyl acrylate and their acidified or quaternized salts, and their mixtures, structure agent: polyethylenically unsaturated monomers (i.e. monomers having at least two unsaturated functional groups), such as, for example, vinyl, preferably allyl, acrylic and epoxy functional groups, for example, methylenebisacrylamide (MBA), triallylamine, tetrallylammonium chloride or by macroinitiators such as the polyperoxides, polyazo compounds and transfer polyagents such as polymercaptan polymers, and their mixtures.

The alkyl groups of the cationic monomer may be linear, cyclic (substituted or not) or branched. They may identical or different. They have a number of carbon atoms preferably comprised between 1 and 10, more preferably between 1 and 8, more preferably between 1 and 4, even more preferably the alkyl group is methyl or ethyl.

Any polymerization process may be used, such as gel polymerization, liquid or emulsion polymerization. The polymer may be obtained in any form, such as a powder, an emulsion, a dispersion, or a solution. The polymer of the invention is preferably water soluble, but also may be water swellable.

The polymer according to the invention is not limited in terms of molecular weight. The polymer has preferably an average molecular weight by weight comprised between 5.000 g/mol and 100.000 g/mol, or an average molecular weight by weight comprised between 100.000 g/mol and 1.000.000 g/mol, or an average molecular weight by weight comprised between 1.000.000 g/mol and 30 million g/mol. The average molecular weight by weight is preferably measured by Gel Permeation Chromatography (GPC).

The present invention also relates to the use of the polymer of the invention in water treatment, sludge dewatering, papermaking process, agriculture, cosmetic and detergency composition, textile process, oil and gas recovery process such as enhanced oil recovery, fracturing, mining operation such as tailings treatment.

The present invention also relates to the use of the polymer of the invention as a dispersant, coagulant, flocculant, thickener, grinding agent, drag reducer, superabsorbent.

The present invention provides a new, unique, highly concentrated and stable composition (preferably a suspension) of dialkyl tin oxide that can be successfully used as catalyst to produce aminoalkyl (meth)acrylate, preferably 2-dimethylaminoethyl (meth)acrylate, by transesterification from an alkyl (meth)acrylates and an amino alcohol.

The new composition of dialkyl tin oxide allows for improving the transesterification reaction. The reaction is simple, less energy consuming, and generates less waste stream. In addition, the productivity of aminoalkyl(meth)acrylate is improved thanks to the use of the new composition because it allows to reduce the induction time and the reaction time. Finally, no fine particles of DBTO (less than 2000 µm, generally less than 1000 µm) are used, thereby solving the risks and health issues for users that manipulate the dialkyl tin oxide.

The particle average diameter in the composition of the invention is preferably comprised between 200 µm and 2000 µm, more preferably between 300 µm and 1500 µm.

The present invention will now be illustrated in greater details with the following examples.

EXAMPLES

Counter-Example 1

Solid DBTO having a Particle Size Distribution of 300 µm is used as a catalyst to produce 2-dimethylaminoethyl acrylate by transesterification of methyl acrylate and dimethylaminoethanol, as described in the document US 2012/0123148.

Counter-Example 2

The same process as counter-example 1 is carried out with solid DBTO having a Particle Size Distribution of 150 µm.

Example According to the Invention

Solid DBTO having a Particle Size Distribution of 300 μm is charged in the wetting cone of a PSU device furnished by SNF, and as described in the document U.S. Pat. No. 8,186,871. A first wetting solution composed of a mixture of methyl acrylate and dimethylaminoethanol (1:1 by weight) is added in the lower part of the wetting cone (the primary inlet circuit), and a second wetting solution, which is the same as the first wetting solution, is sprayed in the grinding chamber to obtain a suspension comprising 85% by weight of dialkyl tin oxide. The resulting suspension is transferred in a vessel and heated at 80° ° C. during 120 minutes with a gentle agitation. The resulting suspension is stable. The dialkyl tin oxide comprised in said suspension is solubilized at a rate of 90% w.

The resulting suspension of DBTO is used as a catalyst to produce 2-dimethylaminoethyl acrylate by transesterification of methyl acrylate and dimethylaminoethanol as described in the document US 2012/0123148.

The reaction parameters are described in Table 1.

TABLE 1

| Reaction parameters | | | |
|---|---|---|---|
| | Induction Time (min) | Reaction Time (h) | Reaction Yield (%) |
| Counter-example 1 | 60 | 10 | 89% |
| Counter-example 2 | 30 | 9.5 | 90% |
| Example | 5 | 8 | 93% |

The particle size reduction in counter-example 2 allows to reduce the induction time and to slightly reduce the reaction time, but creates health issues due to the DBTO powder.

The use of the DBTO composition according to the invention allows to dramatically reduce the induction time, reduce the reaction time by 20%, and leads to a better yield, without the drawback of a powder as in counter-example 2.

Similar performances are observed when methyl methacrylate is replaced by methyl acrylate.

The corresponding monomers obtained according to the process of the invention are quaternized, and used to produce copolymers of acrylamide and quaternized form of aminoalkyl(meth)acrylate (20 mol %/80 mol %). Said polymers are successfully used to flocculate waste water.

The invention claimed is:

1. A dialkyl tin oxide composition comprising:
   about 85% by weight of dibutyl tin oxide, wherein the dibutyl tin oxide has a particle-average diameter of about 300 microns, as measured before being added to the dialkyl tin oxide composition; and
   about 15% by weight of a mixture that is
      about half by weight methyl acrylate; and
      about half by weight dimethylaminoethanol;
the percentages by weight of dibutyl tin oxide and mixture being relative to the weight of the dialkyl tin oxide composition.

2. The dialkyl tin oxide composition according to claim 1, wherein the composition is a suspension in which 70% to 95% by weight of dibutyl tin oxide is solubilized, and 5% to 30% by weight of dibutyl tin oxide is in the form of particles suspended in the composition, the percentages by weight being relative to the weight of dibutyl tin oxide in the dialkyl tin oxide composition.

3. A process for the production of aminoalkyl (meth) acrylate, said process comprising performing a transesterification reaction to form the aminoalkyl (meth)acrylate from an alkyl (meth)acrylates and an amino alcohol, said process comprising using a dialkyl tin oxide composition according to claim 1 as a catalyst of the transesterification reaction.

4. The process according to claim 3, wherein the process comprises the following steps:
   in a reactor, adding at least one amino alcohol, at least one alkyl(meth) acrylate and at least one solvent with a weight ratio of 2-15:2-40:1-5;
   in the same reactor, adding a dialkyl tin oxide composition according to claim 1, with a weight ratio amino alcohol to the dialkyl tin oxide composition ranging from 10:1 to 100:1 to obtain a suspension;
   increasing the temperature of the resulting suspension from 40° C. to 70° ° C., for a period of time from 30 minutes to 500 minutes, for recovering aminoalkyl (meth)acrylate; and
   obtaining aminoalkyl (meth)acrylate.

5. The process according to claim 4, further comprising a step of purifying the aminoalkyl (meth)acrylate.

\* \* \* \* \*